US00PP20609P2

(12) United States Plant Patent
Bauer

(10) Patent No.: US PP20,609 P2
(45) Date of Patent: Dec. 22, 2009

(54) ***COREOPSIS* PLANT NAMED 'ROUTE 66'**

(50) Latin Name: *Coreopsis verticillata*
Varietal Denomination: Route 66

(75) Inventor: Patricia M. Bauer, Lucinda, PA (US)

(73) Assignee: Itsaul Plants, LLC., Alpharetta, GA (US)

( * ) Notice: Subject to any disclaimer, the term of this patent is extended or adjusted under 35 U.S.C. 154(b) by 0 days.

(21) Appl. No.: 12/284,846

(22) Filed: Sep. 25, 2008

(51) Int. Cl.
*A01H 5/00* (2006.01)

(52) U.S. Cl. ..... Plt./417

(58) Field of Classification Search ..... Plt./417
See application file for complete search history.

*Primary Examiner*—June Hwu
(74) *Attorney, Agent, or Firm*—Penny J. Aguirre

(57) ABSTRACT

A new cultivar of *Coreopsis verticillata* named 'Route 66' characterized it's abundant bright yellow inflorescences with a red eye with the red eye coloration of the ray florets spreading to the tips of the petals as they mature and with cooler fall temperatures, its continuous bloom from early summer until frost, its vigorous and robust growth habit, and its cold hardiness to at least U.S.D.A. Zone 5.

2 Drawing Sheets

Botanical classification: *Coreopsis verticillata.*
Variety denomination: 'Route 66'.

BACKGROUND OF THE INVENTION

The present invention relates to a new and distinct cultivar of *Coreopsis* plant, botanically known as *Coreopsis verticillata* 'Route 66' and will be referred to hereinafter by its cultivar name, 'Route 66'. The new cultivar of *Coreopsis* is an herbaceous perennial grown for landscape and container use.

The new invention arose as a naturally occurring whole plant mutation in the Inventor's garden in Lucinda, Pa. in summer of 2005. The parent plants of 'Route 66' are unknown.

Asexual reproduction of the new cultivar was first accomplished by stem cutting under the direction of the Inventor in Alpharetta, Ga. in summer of 2008. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Route 66' as unique from all *Coreopsis* cultivars and species known to the inventor.

1. 'Route 66' exhibits composite inflorescences that are bright yellow in color with a red eye. The red coloration of the ray florets spreads along the veins and in flecks towards the end of the petals as the flowers mature with the petals becoming predominantly red in color with lower average night and day temperatures in fall.
2. 'Route 66' exhibits a vigorous and robust growth habit.
3. 'Route 66' has proven to be hardy at least in U.S.D.A. Zone 5.
4. 'Route 66' exhibits an abundance of inflorescences and blooms continuously from June until frost in Pennsylvania.
5. 'Route 66' exhibits a clump-forming and upright growth habit.

'Route 66' can be most compared to *Coreopsis* 'Autumn Blush' (U.S. Plant Pat. No. 18,184) and *Coreopsis* 'Gold Nugget' (U.S. Plant Pat. No. 19,946). Both exhibit inflorescences that exhibit a red eye on the ray florets. 'Autumn Blush' differs from 'Route 66' in having ray florets that are a pastel orange-yellow color and lightly diffused with red in spring and fall. 'Autumn Blush' is also shorter in plant height. 'Gold Nugget' differs from 'Route 66' in having ray florets with a red eye that remains in the center and does not spread to the rest of the petal, in having ray floret petals that are more notched, and in having a shorter plant height and wider plant spread.

BRIEF DESCRIPTION OF THE DRAWING

The accompanying colored photographs illustrate the overall appearance and distinct characteristics of the new *Coreopsis* as grown outdoors in Alpharetta, Ga. for three months from a 72-cell plug.

The photograph in FIG. 1 provides a view of the habit and foliage of 'Route 66' in bloom.

Figure 1:
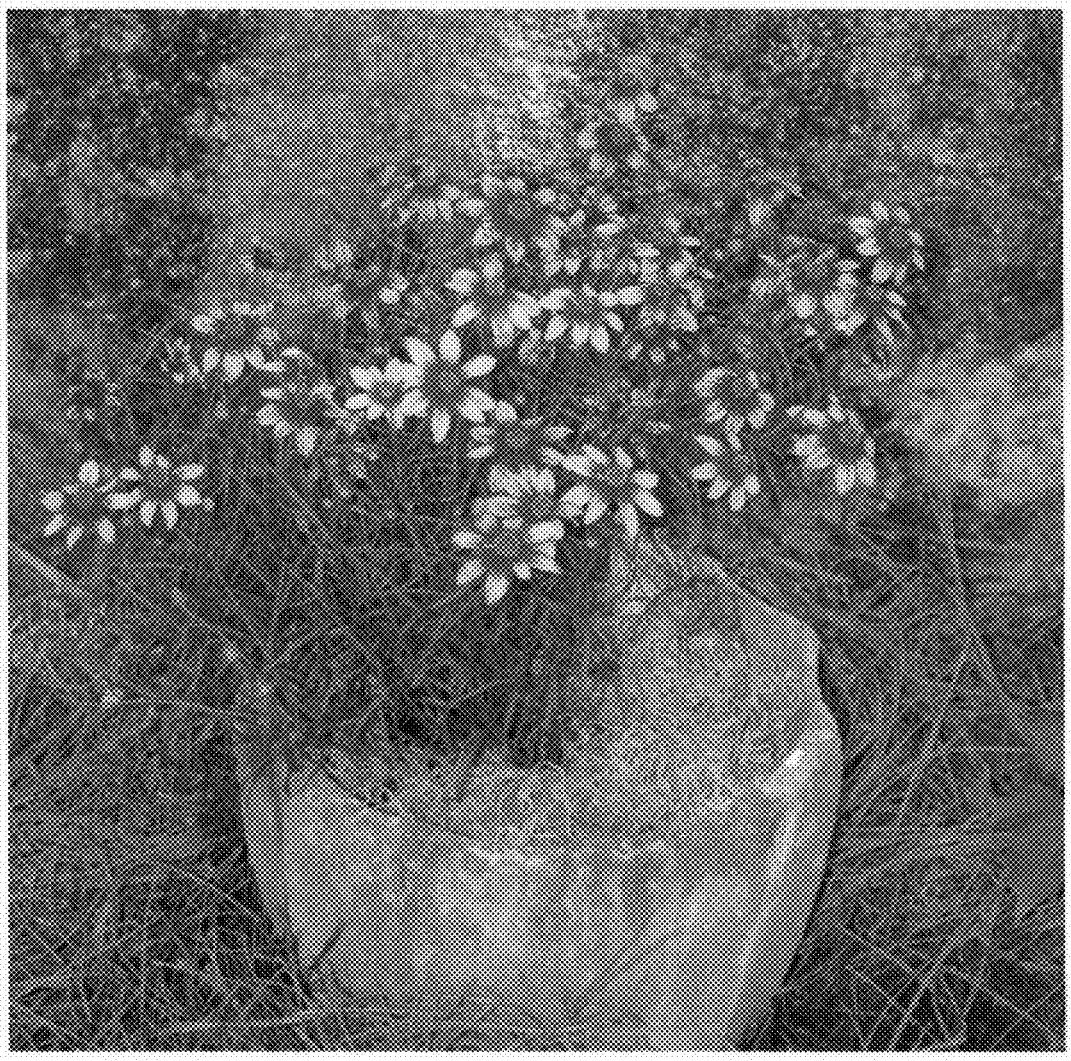
Figure 2:
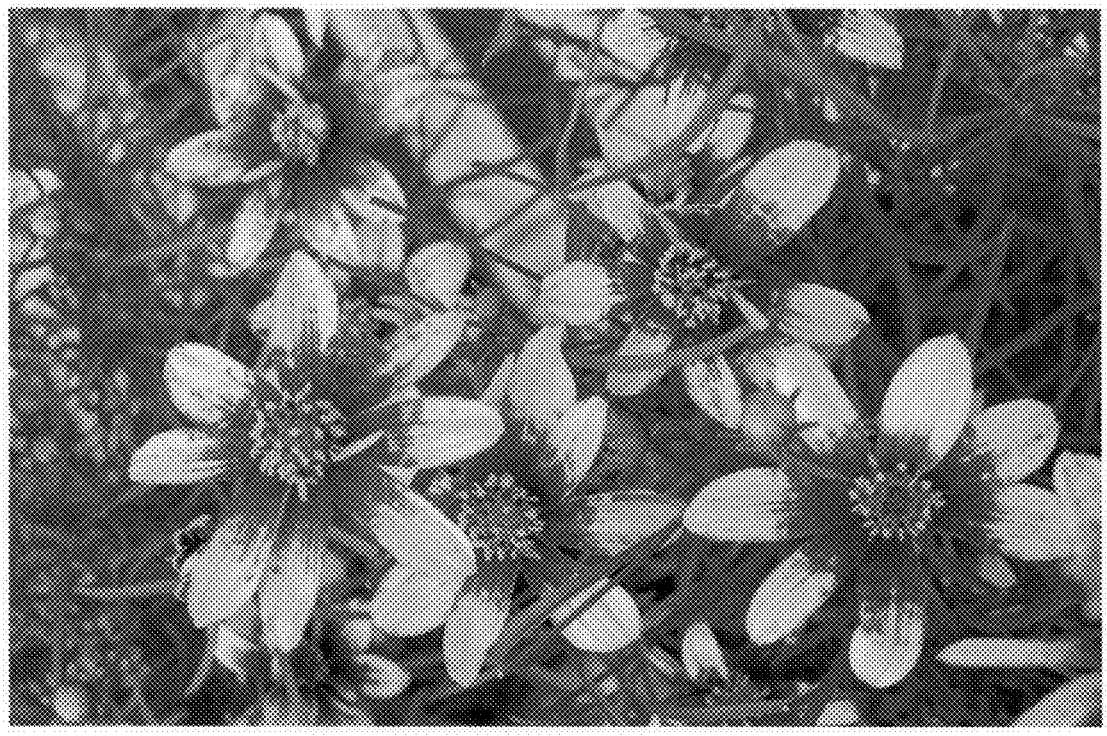

The photograph in FIG. 2 provides a view of a group of inflorescences of 'Route 66'.

Figure 3:
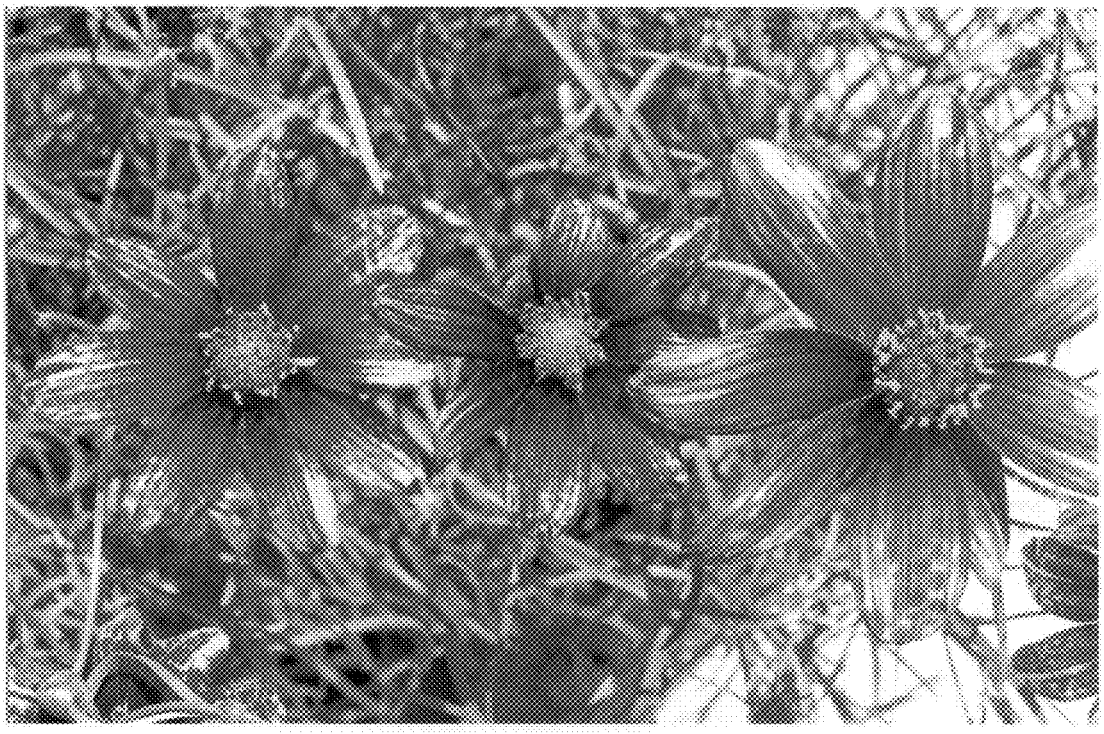

The photograph in FIG. 3 provides a close-up view of a group of inflorescences in fall with lower average day and night temperatures.

The Colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for three years in Pennsylvania and Georgia with the detailed data collected from plants grown outdoors for three months from a 72-cell plug in Alpharetta, Ga. The phenotype of the new cultivar may vary with variations in environmental, climatic, and cultural conditions, as it has not been tested under all possible environmental conditions. The color determination is in accordance with the 2007 R.H.S.

Colour Chart of the Royal Horticultural Society, London, England, except where general color terms of ordinary dictionary significance are used.

General description:

*Blooming period.*—Blooms from June until frost in Pennsylvania.

*Plant habit.*—Herbaceous perennial, clump forming, upright mound, densely branched with abundant blooms.

*Height and spread.*—Reaches 61 to 71 cm (24 to 28 inches) in height and an average of 61 cm (24 inches) in width.

*Cold hardiness.*—At least to U.S.D.A Zone 5, has not been tested in colder regions.

*Diseases resistance.*—No susceptibility or resistance to diseases has been observed.

*Root description.*—Fibrous.

Growth and propagation:

*Propagation.*—Stem cuttings.

*Rooting.*—Root initiation occurs in about 7 days at 75° to 80° F. with a NAA dip and no supplemental lighting or bottom heat, rooted cuttings fully develop in a 72-cell plug in about 3 weeks in May.

*Growth rate.*—Vigorous.

Stem description:

*Shape.*—Tetragonal, solid.

*Stem color.*—New growth; 144A, mature stems; a color between 144A and 138A, woody base; 199B.

*Stem size.*—Main stem; average 19 cm in length with laterals an average of 13 cm in length (excluding peduncles), 2 to 4 cm in width with an average of 2.5 mm in width.

*Stem surface.*—Glabrous, slightly glaucous and finely ridged, develops smooth bark at base when mature.

*Branching habit.*—Freely branched, an average of 9 lateral branches with an average of secondary branches per each lateral branch, branches are opposite in arrangement with an average internode length of 4.2 cm, new lateral flowering branches are continuously produced throughout the summer.

Foliage description:

*Leaf division.*—Simple.

*Leaf margins.*—Typically 5-lobed, deeply dissected into linear lobes.

*Leaf size.*—Up to 5 cm in length and 8.5 cm in width with lobes ranging from 2 to 5 cm in length and an average of 2 mm in width.

*Leaf shape.*—Fan-shaped overall with spreading linear lobes.

*Leaf base.*—Attenuate.

*Leaf apex.*—Narrowly acute.

*Leaf venation.*—Only mid rib is distinguishable, color matches leaf color.

*Leaf arrangement.*—Opposite.

*Leaf quantity.*—30 to 70 per lateral branch.

*Leaf surface.*—Very finely puberulent on upper surface and lower surface.

*Leaf color.*—Young upper surface and lower surface; 137C, mature upper and lower surface; N137A.

Flower description:

*Inflorescence type.*—Campitulum with ray florets surrounding disk florets in the center, forming a radiant head, inflorescences are borne singular to group of 3 at terminals of lateral and secondary branches.

*Lastingness of inflorescence.*—About one week until senescence of ray florets, bracts and disk florets are persistent.

*Fragrance.*—None detected.

*Quantity of inflorescences.*—About 200 open flowers and buds per plant (grown in a one-gallon container at pick bloom.

*Inflorescence size.*—Average 1.2 cm in depth and up to 4.2 cm in diameter when fully open and often become reflexed when mature with an average depth of 2 cm and width of 3 cm, disk portion is an average of 9 mm in diameter.

*Inflorescence buds.*—Average of 9 mm in depth and 7 diameter, shape is spherical, color is a blend of 146B and 153B covered with bracts 144A in color.

*Peduncle.*—Strong, held upright to an angle to about 20% from vertical, average of 6 cm in length and 1 mm in diameter, 137C in color, glabrous surface.

Involucral bracts:

*Bract number.*—Two rows of 8.

*Bract arrangement.*—Outer bracts are un-fused, spreading and held upright somewhat reflexed, inner bracts overlap and surround receptacle, Campanulate in form with apical portion un-fused, spreading, and held close to ray florets.

*Bract size.*—Outer bracts about 4.5 mm in length and 1.5 mm in width, inner bracts about 8 mm in length and 3 mm in width with free portion an average of 4 mm in length and 3 mm in width.

*Bract color.*—Outer bracts N144B on both surfaces, inner bracts; fused portion 144B, un-fused portion N144B.

*Bract texture.*—Outer bract; puberulent, inner bracts waxy.

*Bract apex.*—Outer bract; narrowly acute, inner bracts; acute.

*Bract base.*—Truncate.

*Bract shape.*—Outer bracts; lanceolate, inner bracts; free portion broadly lanceolate.

Ray florets (sterile):

*Number.*—8.

*Shape.*—Elliptic to slightly Oblanceolate.

*Size.*—Average of 2 cm in length and 9 mm in width.

*Apex.*—Broadly acute.

*Base.*—Broadly cuneate.

*Margins.*—Entire and sometimes emarginate at apex.

*Aspect.*—Spreading, variable but primarily horizontal and often reflexed when mature.

*Texture.*—Glabrous on both surfaces.

*Color.*—Upper surface when fully open; 6A with an eye (about 7 mm in length) of 59A to 59B and flecks and veining of 59B extending towards apex, lower surface when fully open; 6A and diffused with 166A primarily towards base, upper surface when maturing; 11A with an eye (about 1 cm) 59A to 59B and heavily speckled with 59A to 59B toward apex with an average of 75% of the petal area 59A to 59B with greater mottling occurring with lower temperatures in fall, lower surface when maturing; 11A and very lightly diffused with 177A with some specks of 59A at base.

Disk florets (male and female):

*Shape.*—Tubular, corolla is fused, flared at apex.

*Size.*—About 8 mm in length and 1.1 mm in width.

*Color.*—In masse; 14A when fully open and becoming 200B when dried and ray florets drop, corolla; 4A in color and translucent.

*Receptacle.*—About 3 mm in diameter and 2 mm in depth, 146A in color.

Reproductive organs:

*Presence.*—Disk florets are perfect, ray flowers are sterile.

*Gynoecium.*—1 Pistil, 4 mm in length, style is very fine and about 7C in color and translucent, bifid pilose stigma is 14A in color with branches about 1.5 mm in length and recurved, ovary is 2.5 mm in length, 1 mm in width, inferior, and 7D in color.

*Androcoecium.*—5 stamens, fused into tube surrounding style, 2.2 mm in length and 0.7 mm in width, about 200A in color, pollen was not present or distinguishable.

*Fruit.*—No fruit development has been observed.

It is claimed:

1. A new and distinct cultivar of *Coreopsis* plant named 'Route 66' as herein illustrated and described.

* * * * *